United States Patent
Williams et al.

(10) Patent No.: US 12,343,559 B2
(45) Date of Patent: Jul. 1, 2025

(54) DEVICE AND METHOD FOR BLUE LIGHT MODULATION OF BRAIN INFLAMMATION

(71) Applicant: Wisconsin Alumni Research Foundation, Madison, WI (US)

(72) Inventors: Justin Williams, Cambridge, WI (US); Jyoti J Watters, Madison, WI (US); Kevin P. Cheng, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/208,654

(22) Filed: Jun. 12, 2023

(65) Prior Publication Data

US 2023/0338745 A1 Oct. 26, 2023

Related U.S. Application Data

(62) Division of application No. 15/013,149, filed on Feb. 2, 2016, now abandoned.

(51) Int. Cl.
*A61N 5/06* (2006.01)

(52) U.S. Cl.
CPC ......... *A61N 5/0624* (2013.01); *A61N 5/0601* (2013.01); *A61N 2005/0612* (2013.01); *A61N 2005/0626* (2013.01); *A61N 2005/0663* (2013.01)

(58) Field of Classification Search
CPC .............................. A61N 5/06; A61N 5/0622
See application file for complete search history.

(56) References Cited

U.S. PATENT DOCUMENTS

| 2006/0100679 A1* | 5/2006 | DiMauro | A61N 5/0601 607/94 |
| 2012/0253261 A1* | 10/2012 | Poletto | A61M 5/14276 604/20 |
| 2016/0144196 A1* | 5/2016 | Gilson | A61B 34/30 601/3 |

* cited by examiner

*Primary Examiner* — Lynsey C Eiseman
(74) *Attorney, Agent, or Firm* — Boyle Fredrickson, S.C.

(57) ABSTRACT

A device and method are provided for modulating brain inflammation. The device includes a light source positionable at a location adjacent a portion of brain for modulating the inflammation thereof. The light source has a first off condition and second on condition wherein the light source generates light having a wavelength in the range of 450-495 nanometers (nm). A controller is operatively connected to the light source. The controller provides control signals to the light source for controlling the switching of the light source between the on and the off conditions. The controller is configured to switch the light source to the on condition for a portion of a treatment cycle.

14 Claims, 6 Drawing Sheets

DEVICE AND METHOD FOR BLUE LIGHT MODULATION OF BRAIN INFLAMMATION

CROSS-REFERENCE TO RELATED APPLICATION

This application is a divisional of U.S. patent application Ser. No. 15/013,149; filed on Feb. 2, 2016, entitled "Device and Method for Blue Light Modulation of Brain Inflammation"; the contents of which is incorporated herein by reference in its entirety.

REFERENCE TO GOVERNMENT GRANT

This invention was made with government support under N66001-12-C-4025 awarded by the US Navy and HL111598 awarded by the National Institutes of Health. The government has certain rights in the invention.

FIELD OF THE INVENTION

This invention relates generally to the treatment of brain injury and inflammation, and in particular, to a device and method for blue light modulation of brain inflammation.

BACKGROUND AND SUMMARY OF THE INVENTION

Microglia, otherwise known as brain macrophages, are central nervous system (CNS) resident immune cells of yolk sac origin. A large number of microglial studies over the past two decades have revealed that these cells play an intricate role in nearly every aspect of neurological function, development, and disease. Microglial inflammatory activities have been implicated in virtually all neurological injuries and diseases including psychiatric disorders, such as schizophrenia and depression. Following CNS insult, microglia display an activated morphology and produce pro-inflammatory cytokines, such as interleukin 1 beta (IL-1β) and tumor necrosis factor alpha (TNFα), as well as other pro-inflammatory molecules including nitric oxide (produced by inducible nitric oxide synthase; iNOS) and prostaglandins (produced by cyclooxygenase-2; COX-2). In parallel, microglia also produce a number of anti-inflammatory and neuroprotective/trophic factors such as interleukin-10 (IL-10), transforming growth factor beta (TGF-β), vascular endothelial growth factor (VEGF), and insulin-like growth factor (IGF-1) which activate pro-survival pathways and limit the magnitude of the damaging inflammatory response. Microglia also produce interleukin-6 (IL-6) which, while often considered to be pro-inflammatory, also has neurotrophic-like, and anti-inflammatory regulatory roles in the CNS.

Although acute microglial activation is a necessary aspect of the tissue reparative response to injury and foreign pathogens, when their inflammatory activities become dysregulated, a state of continued activation and chronic neuroinflammation results, even though the initial insult has subsided. This chronic activation state leads to exaggerated neuronal death and dysfunction of neural circuits which has made microglia of particular interest in neurodegenerative diseases, such as Alzheimer's and Parkinson's diseases, and amyotrophic lateral sclerosis (ALS) wherein pro-inflammatory cytokines are thought to contribute to disease progression. These observations have led to efforts targeting neuroinflammation as a therapeutic modality with which to treat neurodegenerative diseases. They also underscore the need for new tools to manipulate and study these processes.

Blue light has become a routinely applied tool used across multiple disciplines with the advent of fluorescence microscopy and fluorescence assisted assays. Additionally, recent advances in optogenetic tools over the past decade have led to a dramatic increase in the use of blue light in non-fixed, live in vitro and in vivo applications, especially in neuroscience. However, relatively little is known about the potential side effects of these levels of blue light on non-neuronal CNS cell types, including microglia, that do not express optogenetic proteins. To date, the majority of studies utilizing blue light in a non-imaging or non-optogenetic application have focused on its use as a germicidal agent or in targeted carcinoma ablation. These studies typically use high intensity and long duration exposures to deliver a high energy dose of light. In parallel, literature reports and clinical trials have suggested that red and near-infrared (NIR) light have many therapeutic effects in their own right, across a range of conditions including wound healing, arthritis, myocardial infarction, and multiple neuropathologies.

Therefore, it is a primary object and feature of the present invention to provide a device and method for blue light modulation of brain inflammation.

It is a still further object and feature of the present invention to provide a device and method for blue light modulation of brain inflammation to treat neurodegenerative diseases and any disorder in which excessive microglial inflammatory activities is a hallmark.

It is a further object and feature of the present invention to provide a device and method for blue light modulation of brain inflammation that is simple to utilize and implement.

In accordance with the present invention, a device is provided for modulating brain inflammation. The device includes a light source positionable at a location adjacent to a portion of brain for modulating the inflammation thereof. The light source has a first off condition and second on condition wherein the light source generates light having a wavelength in the range of 450-495 nanometers (nm). A controller is operatively connected to the light source. The controller provides control signals to the light source for controlling the switching of the light source between the on and the off conditions. The controller is configured to switch the light source to the on condition for a portion of a treatment cycle.

The treatment cycle may be a first of a plurality of treatment cycles and the controller may be configured to switch each of the plurality of light sources to the on condition for the portion of each treatment cycle. The brain includes an outer surface and the light source may be spaced from the outer surface of the brain. Alternatively, the light source may abut the outer surface of the brain or at least a portion of the light source may be positionable within the brain. If the light source is one of a plurality of light sources, each of the plurality of light sources is operatively connected to the controller and has a first off condition and second on condition wherein each of the light sources generates light having a wavelength in a range, e.g. 450-495 nanometers (nm). The controller provides control signals to the plurality of light sources for controlling the switching of the plurality of light sources between the on and the off conditions. The controller is configured to switch the plurality of light sources to the on condition for a portion of a treatment cycle. In addition, the controller may be configured to simultaneously switch the plurality of light sources between the on condition and the off condition.

In accordance with a further aspect of the present invention, a method of modulating brain inflammation is provided. The method includes the step of positioning a light source adjacent a brain. The light source has a first off condition and a second on condition wherein the light source generates light having a wavelength in the range of 450-495 nanometers (nm). The light source is switched to the on condition for a first portion of a treatment cycle.

The method may include the additional steps of switching of the light source from the on condition to the off condition for a second portion of the treatment cycle and repeating the step of switching of the light source to the on condition for the first portion of a treatment cycle for a plurality of treatment cycles. The light source may be positioned at a location spaced from an outer surface of the brain. Alternatively, the light source may be positioned at a location abutting an outer surface of the brain or at a location wherein at least a portion of the light source is received within the brain. The light source may be one of a plurality of light sources and the method may include the additional step of switching each of the plurality of light source to the on condition for the first portion of a treatment cycle. The plurality of light sources may be switched simultaneously to the on condition.

In accordance with a still further aspect of the present invention, a method of modulating brain inflammation is provided. The method includes the steps of generating light having a wavelength in the range of 450-495 nanometers (nm) and directing the light at a portion of the brain for a treatment cycle.

The step of directing the light at the portion of the brain may be repeated for a plurality of additional treatment cycles. In addition, it is contemplated to terminate the generation of the light for a portion of the treatment cycle. The light is generated by a light source positioned at a location spaced from an outer surface of the brain.

Alternatively, the light source may be positioned at a location abutting an outer surface of the brain or at a location wherein at least a portion of the light source is received within the brain. It is further contemplated for the light to be generated by a plurality of light sources and for the plurality of light sources simultaneously generate the light.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
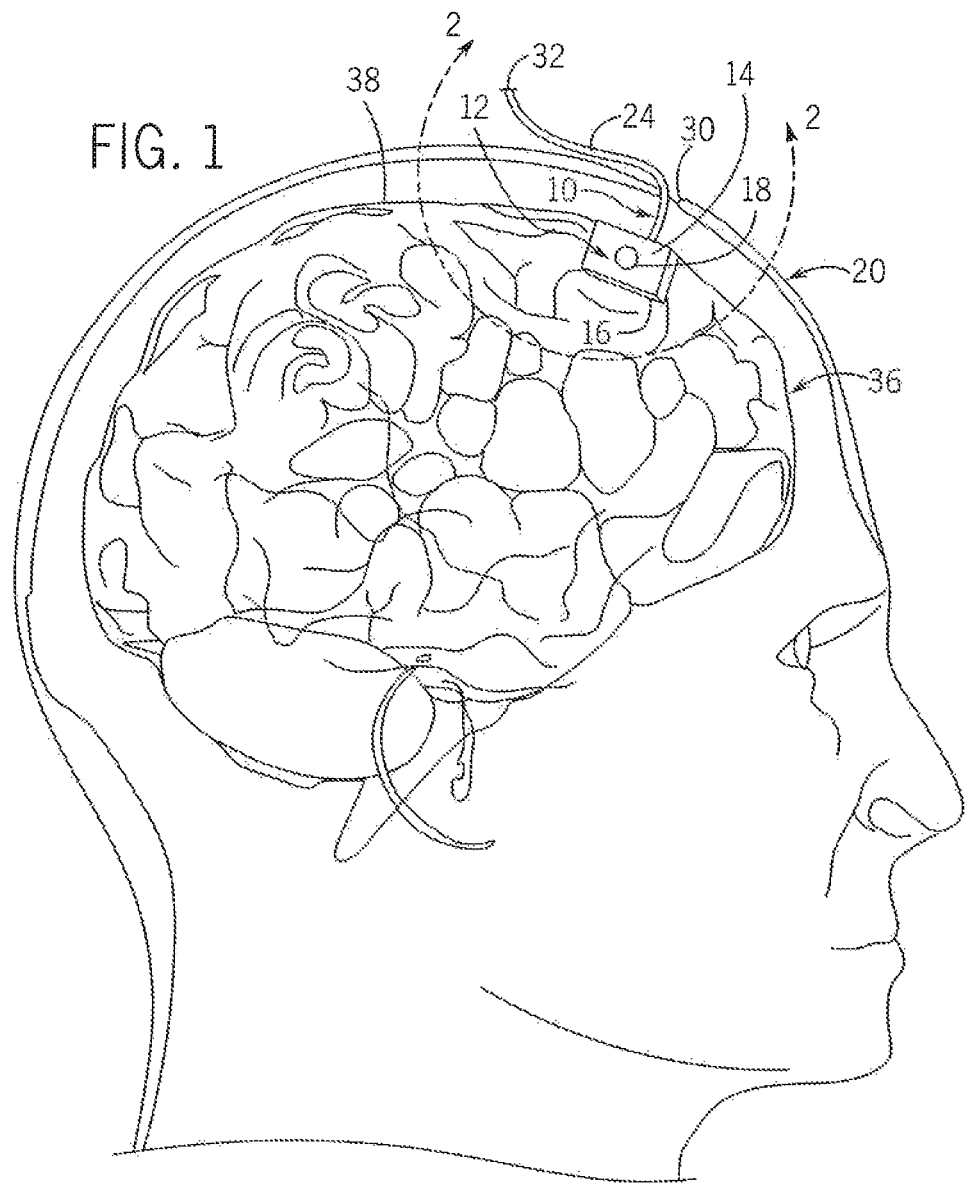
FIG. 1 is an isometric view of a device for blue light modulation of brain inflammation implanted on a surface of a human brain in accordance with the present invention.

Referring to FIG. 1, an exemplary configuration of a device for blue light modulation of brain inflammation in accordance with the present invention is generally designated by the reference numeral 10. In the depicted embodiment, device 10 includes base 12 having a generally square configuration. However, other configurations of base 10 are possible without deviating from the scope of the present invention. It is contemplated to fabricate base 12 from a flexible, biocompatible polymer to provide an optimal implant environment and extend the time period that device 10 may be maintained within cranium 20 without inducing excessive foreign body or immune responses. Further, it can be appreciated device 10 may be adapted for implantation on the surface of other parts of a body, both internal (such as a spinal cord) and external, without deviating from the scope of the present invention.

Figure 2:
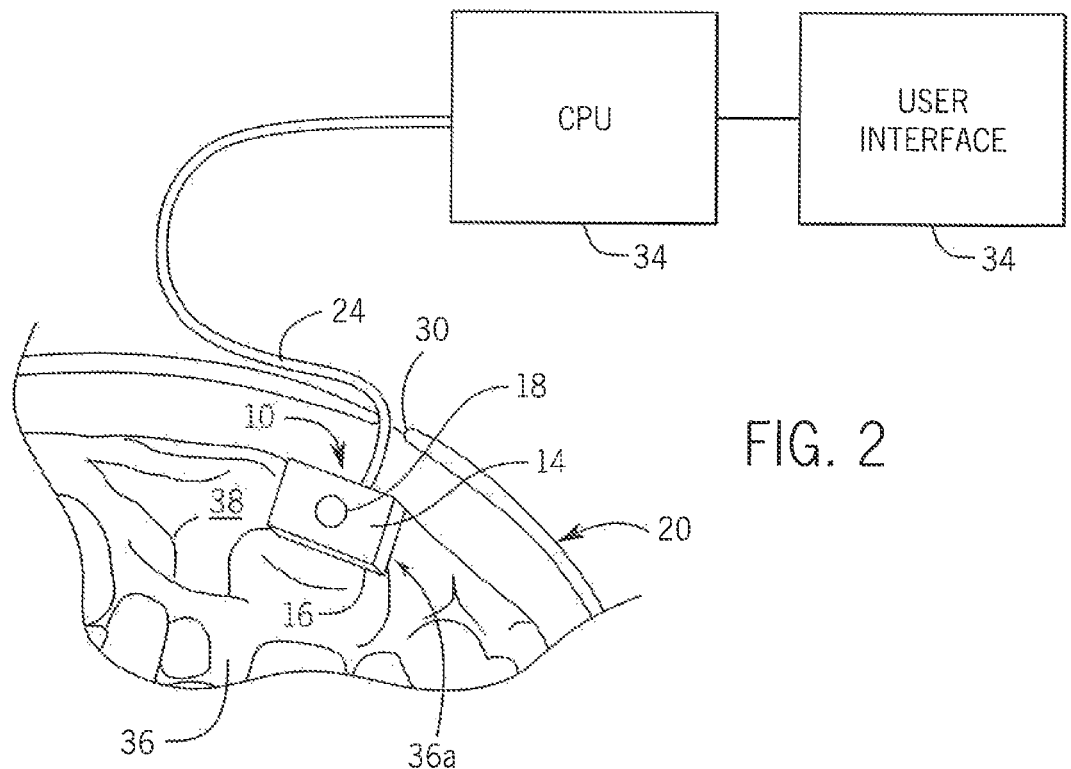
FIG. 2 is an enlarged, isometric view of the device for blue light modulation of brain inflammation of the present invention taken along line 2-2 of FIG. 1.

Base 12 includes upper and lower surfaces 14 and 16, respectively. Light source 18 is provided in lower surface 16 of base 12. For reasons hereinafter described, light source 18 may be switched or toggled between a first off condition wherein light source 18 generates no light and a second on condition wherein light source 18 generates blue light having a wavelength in the range of 450-495 nanometers (nm). Further, by varying the power supplied to light source 18, the intensity of the light supplied by light source 18 may be varied in a conventional manner. Other parameters of the light supplied, i.e. pulse width, duty cycle, etc., may also be varied in a conventional manner. Light source 18 is operatively connected to lead wire 24 which extends through base 18 and projects from upper surface 14 of base 12. Lead wire 24 terminates at terminal end 32 which is connectable to central processing unit (CPU) 34, FIG. 2, for reasons hereinafter described. Alternatively, it can be appreciated that light source 18 may be wirelessly connected to CPU 34. CPU 34 may, in turn, be operatively connected to user interface 35 to set various parameters to facilitate the controlled delivery of blue light to desired portion 36a of brain 36. Alternately, CPU 36 may be implanted with a body and be in wireless communication with user interface 35 through conventional means.

As previously noted, in order to treat brain injury and inflammation, it is contemplated to provide for the controlled delivery of blue light to desired portion 36a of brain 36. More specifically, in operation, device 10 is inserted though opening 30 in cranium 20 of an individual such that lower surface 16 of base 12 is positioned against outer surface 38 of brain 36. Apertures (not shown) may extend through base 12 of device 10 to make device 10 porous, and as such, increase the biocompatibility between device 10 and brain 36. Further, it is contemplated to provide chemicals, drugs or other stimuli within such apertures to further enhance the biocompatibility of device 10 and brain 36.

With device 10 positioned, it is contemplated to direct blue light at desired portion 36a of brain 36. By way of example, it is contemplated for a user to interact with user interface 35 so as to provide instructions for the operation of device 10. More specifically, the user may pre-select: 1) a desired intensity of the blue light directed at desired portion 36a of brain 36; 2) a length of a treatment cycle; 3) a desired portion of the treatment cycle to which the blue light is directed at the desired portion of brain 36; 4) a number of treatment cycles to be performed and/or a desired treatment period in which the treatment cycle is repeated; and 5) other parameters associated with light delivery such as pulse width, duty cycle, etc., that are generally known in the field.

In response to the instructions provided by the user, CPU 34 executes a computer program stored thereon and provides signals along lead wire 24 to toggle light source 18 between the on condition and the off condition and to control the intensity of the blue light source supplied by the light source 18. By way of example, it is contemplated for CPU 34 direct blue light at the desired portion of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours).

It has been found that low levels of blue light delivered in short, repetitive, low level doses alters the basal expression of inflammatory and neurotrophic genes in both immortalized and primary microglia. Further, blue light delivered at these doses strongly reduces inflammatory gene expression in lipopolysaccharide (LPS)-activated microglia in the absence of significant changes in cell viability, apoptosis, or DNA damage. As is known, the inflammatory genes heretofore described play significant roles in promoting neuronal death and injury in a number of inflammatory, degenerative and traumatic injuries. Thus, by applying an optimized intensity of blue light in optimized doses to desired portion 36a of brain 36 (or CNS) to attenuate expression of these the inflammatory genes, modulation of microglial activities in desired portion 36a of brain 36 may be achieved. This modulation provides significant therapeutic benefits in a host of CNS disorders.

Figure 3:
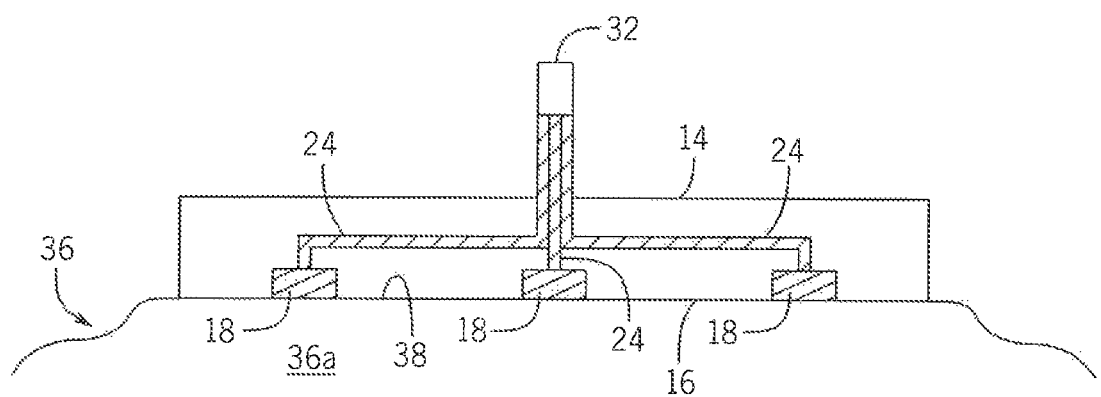
FIG. 3 is an enlarged, cross sectional view, showing the device of FIGS. 1-2 incorporating an array of light sources.

Alternatively, it is contemplated for device 10 to include an array of light sources 18 in lower surface 16 of base 12, FIG. 3, in order to optimize the intensity and dosage of blue light supplied to desired portion 36a of brain 36. Each light source 18 of the array of light sources may be individually switched or toggled between a first off condition wherein each light source 18 generates no light and a second on condition wherein light source generates blue light having a wavelength in the range of 450-495 nanometers (nm). Each light source 18 of the array of light sources is operatively connected to a corresponding lead wire 24 which extends through base 12 and projects from upper surface 14 of base 12. Each lead wire 24 terminates at terminal end 32 which is connectable to central processing unit (CPU) 34, for reasons hereinafter described.

With device 10 positioned, it is contemplated to direct blue light at the desired portion of brain 36. As previously described, it is contemplated for a user to interact with user interface 35 so as to provide instructions for the operation of device 10. For example, the user may pre-select: 1) a desired intensity of the blue light directed at desired portion 36a of brain 36; 2) a length of a treatment cycle; 3) a desired portion of the treatment cycle to which the blue light is directed at the desired portion of brain 36; 4) a number of treatment cycles to be performed and/or a desired treatment period in which the treatment cycle is repeated; and 5) other parameters associated with light delivery such as pulse width, duty cycle, etc., that are generally known in the field. In addition, it is contemplated for the user to pre-select the order of actuation of each light source 18 of the array of light sources. In other words, the user may choose to toggle all of light sources 18 of the array of light sources to the on condition: 1) simultaneously; 2) sequentially; or 3) in a user selected order.

In response to the instructions provided by the user, CPU 34 executes a computer program stored thereon and provides signals along lead wire 24 to toggle each light source 18 of the array of light sources between the on condition and the off condition and to control the intensity of the blue light source supplied by each light source 18 of the array of light sources. Each light source 18 of the array of light sources may be toggled simultaneously or may toggled individually in accordance with the user specified instructions. For example, it is contemplated for CPU 34 to toggle each light source 18 of the array of light sources to direct blue light at desired portion 36a of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours). Alternatively, CPU 34 may toggle each light source 18 of the array of light sources individually such that each light source 18 directs blue light at desired portion 36a of brain 36 at a desired intensity (e.g. between 0 and 100 mJ/cm$^2$·min) for a desired portion (e.g. 1 second) of a treatment cycle (e.g. 1 minute) independently of the other light sources 18 of the array of light sources. The process may be repeated for a desired treatment period (e.g. 6 hours).

Figure 4:
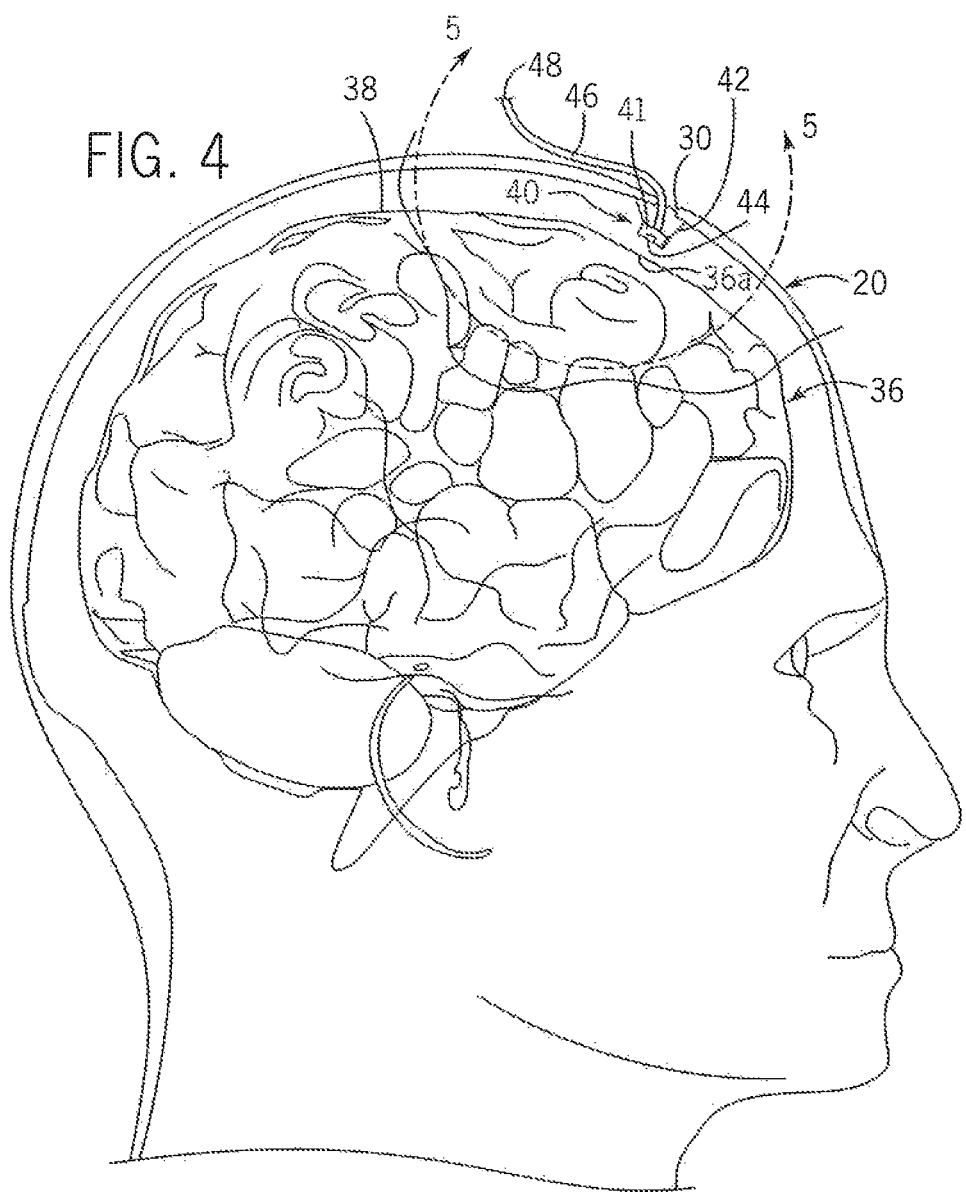
FIG. 4 is an isometric view of an alternate embodiment of a device for blue light modulation of brain inflammation supported above on a surface of a human brain in accordance with the present invention.
Figure 5:
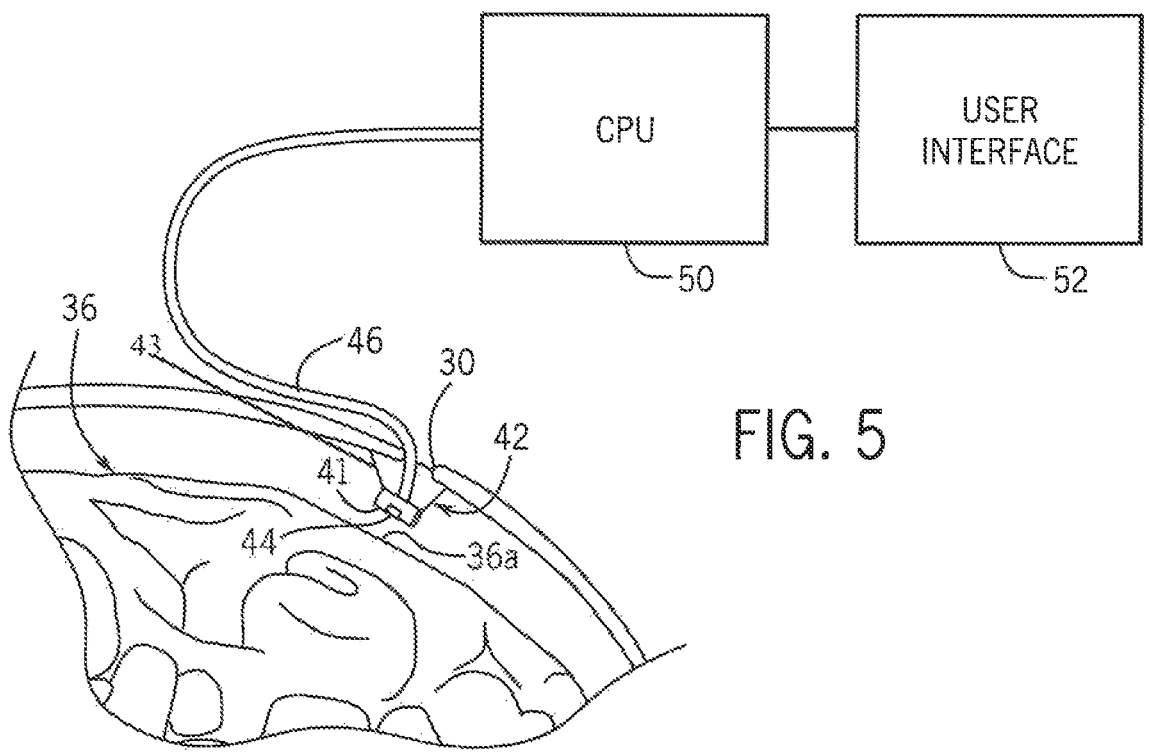
FIG. 5 is an enlarged, isometric view of the device for blue light modulation of brain inflammation of the present invention taken along line 5-5 of FIG. 4.

Referring to FIG. 4, an alternate embodiment of a device for blue light modulation of brain inflammation in accordance with the present invention is generally designated by the reference numeral 40. In the depicted embodiment, device 40 includes support 42 having light source 44 mounted within lower surface 41 thereof. Support 42 further includes projection 43 projecting from the outer surface thereof. Projections 43 are configured to engage an inner surface of cranium 20 and space support 42 from cranium 20 when support 42 is received in cranium 20 and spaced from the outer surface of the brain 36. Light source 44 may be switched or toggled between a first off condition wherein light source 44 generates no light and a second on condition wherein light source 44 generates blue light having a wavelength in the range of 450-495 nanometers (nm). Further, by varying the power supplied to light source 44, the intensity of the light supplied by light source 44 may be varied. Light source 44 may be wirelessly connectable to central processing unit (CPU) 50 or operatively connected to lead wire 46 which terminates at terminal end 48 which is connectable to CPU 50, FIG. 5, for reasons hereinafter described. CPU 50 may, in turn, be wirelessly connectable to user interface 52 in a conventional manner or operatively connected to user interface 52 in order to allow a user to set various parameters to facilitate the controlled delivery of blue light to desired portion 36a of brain 36.

In order to treat brain injury and inflammation, it is contemplated for device 40 to provide the controlled delivery of blue light to desired portion 36a of brain 36. More specifically, in operation, device 40 is inserted though opening 30 in cranium 20 of an individual and fixated at a location wherein light source 44 is directed at a desired portion of brain 36 to be treated. The user interacts with user interface 35 so as to provide instructions for the operation of device 40. More specifically, the user may pre-select: 1) a desired intensity of the blue light directed at desired portion 36a of brain 36; 2) a length of a treatment cycle; 3) a desired portion of the treatment cycle to which the blue light is directed at the desired portion of brain 36; 4) a number of treatment cycles to be performed and/or a desired treatment period in which the treatment cycle is repeated; and 5) other parameters associated with light delivery such as pulse width, duty cycle, etc., that are generally known in the field. In response to the instructions provided by the user, CPU 50 executes a computer program stored thereon and provides signals along lead wire 46 to toggle light source 44 between the on condition and the off condition and to control the intensity of the blue light source supplied by the light source 44. By way of example, it is contemplated for CPU 50 to toggle light source 44 between the on and off conditions so as to direct blue light at desired portion 36a of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours).

Figure 6:
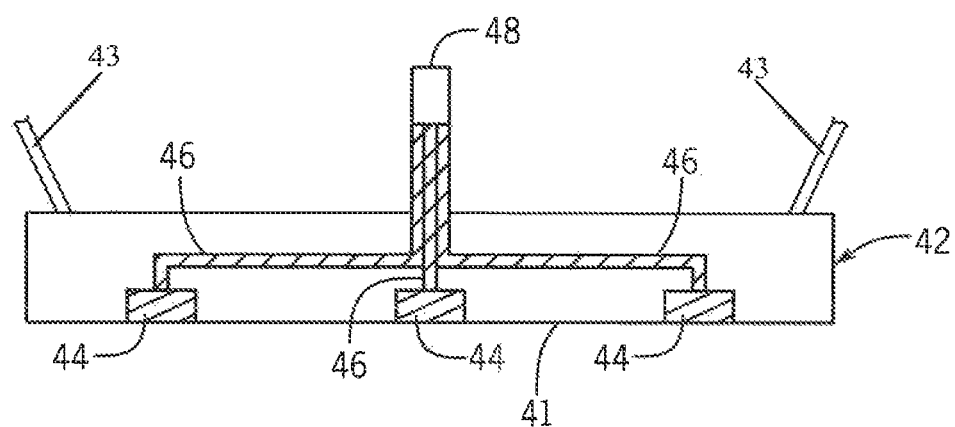
FIG. 6 is an enlarged, cross sectional view, showing the device of FIGS. 4-5 incorporating an array of light sources.

Alternatively, it is contemplated to operatively connect an array of light sources 44 to support 42, FIG. 6, in order to optimize the intensity and dosage of blue light supplied to desired portion 36a of brain 36. Each light source 44 of the array of light sources may be individually switched or toggled between a first off condition wherein light source 44 generates no light and a second on condition wherein light source generates blue light having a wavelength in the range of 450-495 nanometers (nm). Each light source 44 of the array of light sources is operatively connected to lead wire 46 terminates at terminal end 48 which is connectable to central processing unit (CPU) 50, for reasons hereinafter described.

As previously described, it is contemplated for a user to interact with user interface 35 so as to provide instructions for the operation of device 10. For example, the user may pre-select: 1) a desired intensity of the blue light directed at desired portion 36a of brain 36; 2) a length of a treatment cycle; 3) a desired portion of the treatment cycle to which the blue light is directed at the desired portion of brain 36; 4) a number of treatment cycles to be performed and/or a desired treatment period in which the treatment cycle is repeated; and 5) other parameters associated with light delivery such as pulse width, duty cycle, etc., that are generally known in the field. In addition, it is contemplated for the user to pre-select the selected actuation of each light source 44 of the array of light sources. In other words, the user may select to toggle light sources 44 of the array of light sources to the on condition: 1) simultaneously; 2) sequentially; or 3) in a user selected order.

In response to the instructions provided by the user, CPU 50 executes a computer program stored thereon and provides signals along lead wire 46 to toggle each light source 44 of the array of light sources between the on condition and the off condition and to control the intensity of the blue light source supplied by each of the light sources 44. Each light source 44 of the array of light sources may be toggled simultaneously or may toggled individually. For example, it is contemplated for CPU 50 to toggle each light source 44 of the array of light sources to direct blue light at desired portion 36a of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours). Alternatively, CPU 50 may selectively toggle each light source 44 of the array of light sources individually so as to direct blue light at the desired portion of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours).

Figure 7:
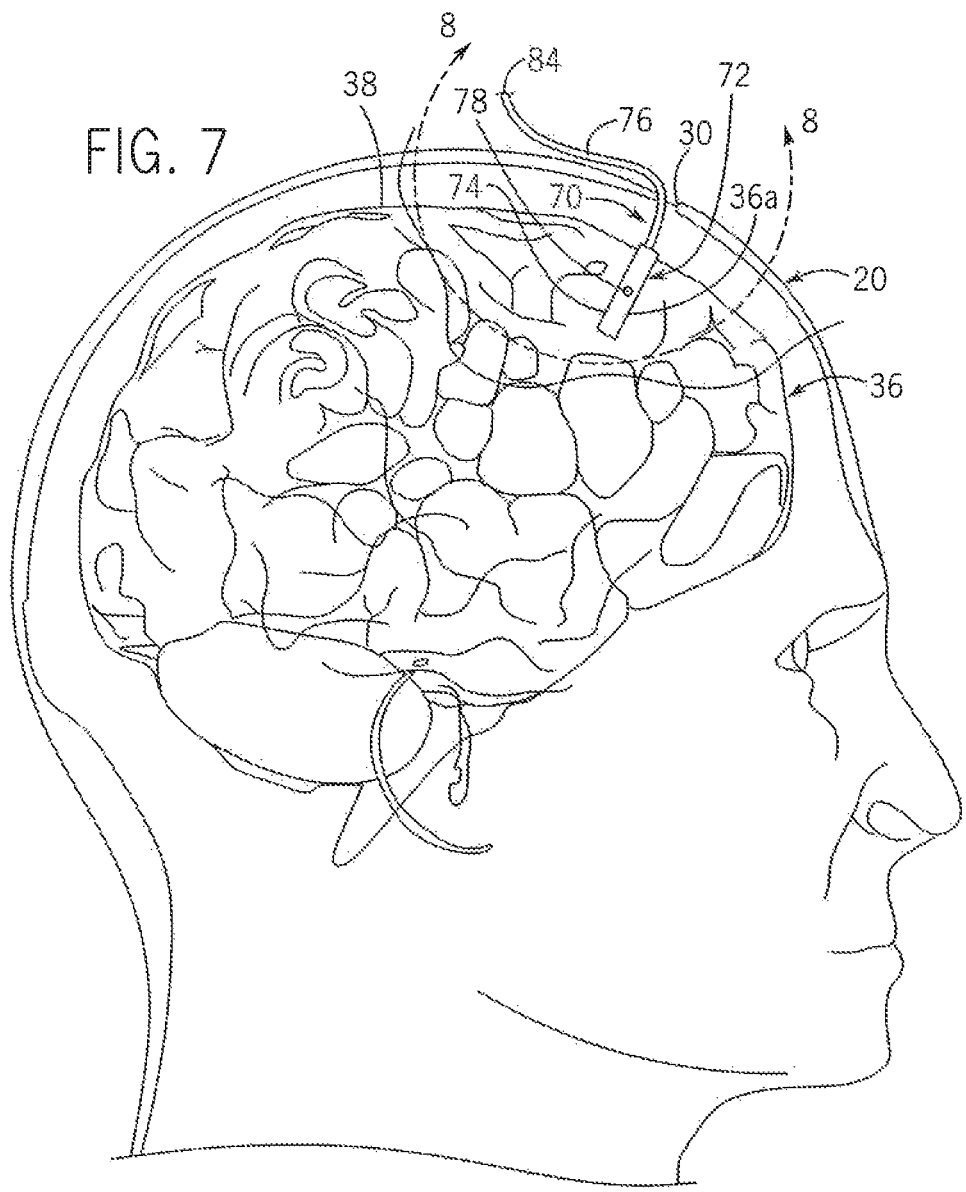
FIG. 7 is an isometric view of a still further alternate embodiment of a device for blue light modulation of brain inflammation inserted into a human brain in accordance with the present invention.
Figure 8:
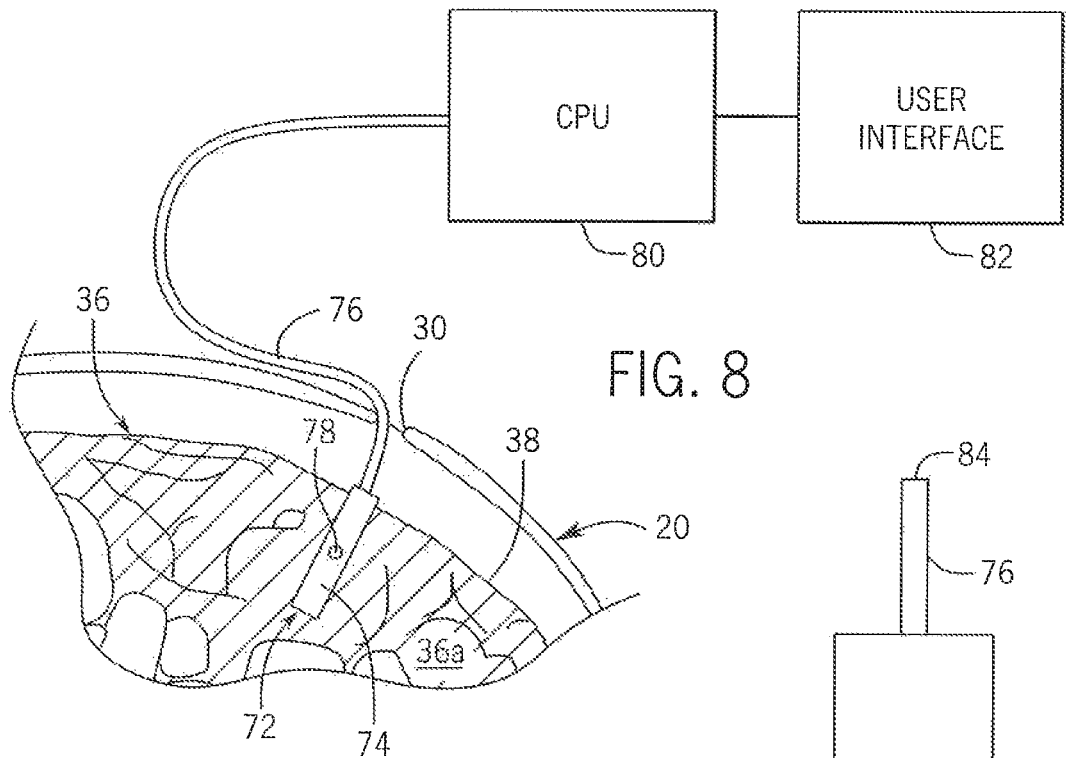
FIG. 8 is an enlarged, isometric view of the device for blue light modulation of brain inflammation of the present invention taken along line 8-8 of FIG. 7.

Referring to FIG. 7, a further embodiment of a device for blue light modulation of brain inflammation in accordance with the present invention is generally designated by the reference numeral 70. In the depicted embodiment, device 70 includes an elongated neural probe 72 having a generally cylindrical outer surface 74. However, other configurations of neural probe 72 are possible without deviating from the scope of the present invention. Light source 78 is provided in outer surface 74 of neural probe 72. For reasons hereinafter described, light source 78 may be switched or toggled between a first off condition wherein light source 78 generates no light and a second on condition wherein light source 78 generates blue light having a wavelength in the range of 450-495 nanometers (nm). Further, by varying the power supplied to light source 78, the intensity of the light supplied by light source 78 may be varied. Light source 78 is operatively connected to lead wire 76 which terminates at terminal end 84 which is connectable to central processing unit (CPU) 80, for reasons hereinafter described. CPU 80 may, in turn, be operatively connected to user interface 82 to set various parameters to facilitate the controlled delivery of blue light to desired portion 36a of brain 36.

In operation, device 70 is inserted though opening 30 in cranium 20 of an individual and into brain 36 through outer surface 38 thereof such that light source 78 is adjacent desired portion 36a of brain 36. With device 70 positioned, it is contemplated to direct blue light at desired portion 36a of brain 36. More specifically, the user interacts with user interface 82 in order to provide instructions for the operation of device 70. The user may pre-select: 1) a desired intensity of the blue light directed at desired portion 36a of brain 36; 2) a length of a treatment cycle; 3) a desired portion of the treatment cycle to which the blue light is directed at the desired portion of brain 36; and 4) a number of treatment cycles to be performed and/or a desired treatment period in which the treatment cycle is repeated. In response to the instructions provided by the user, CPU 80 executes a computer program stored thereon and provides signals along lead wire 76 to toggle light source 78 between the on condition and the off condition and to control the intensity of the blue light source supplied by the light source 78. By way of example, it is contemplated for CPU 80 direct blue light at the desired portion of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours).

It is contemplated to combine device 70 of the present invention with a conventional electrode, e.g. one used in connection with deep brain stimulation methods to treat Parkinson's disease patients. By incorporating device 70 in such electrode, the functionality of the electrode may be extended by minimizing the microglial and inflammatory tissue responses in the area around the electrode, thereby extending the time of therapeutic utility of the electrode. Further, such an arrangement allows for the delivery of anti-inflammatory light paradigms to targeted volumes of neural tissue, thereby circumventing the problems associated with systemic drug delivery and CNS penetrance.

Figure 9:
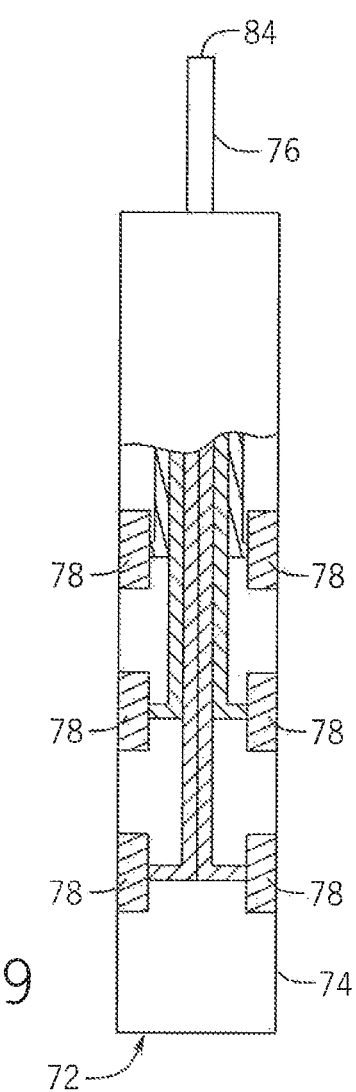
FIG. 9 is an enlarged, cross sectional view, showing the device of FIGS. 7-8 incorporating an array of light sources.

Alternatively, it is contemplated for device 70 to include an array of light sources 78 in outer surface 74 of neural probe 72, FIG. 9, in order to optimize the intensity and dosage of blue light supplied to desired portion 36a of brain 36. Each light source 78 of the array of light sources may be individually switched or toggled between a first off condition wherein each light source 78 generates no light and a second on condition wherein light source generates blue light having a wavelength in the range of 450-495 nanometers (nm). Each light source 78 of the array of light sources is operatively connected to lead wire 76 terminates at terminal end 84 which is connectable to central processing unit (CPU) 80, for reasons hereinafter described.

As previously described, it is contemplated for a user to interact with user interface 82 so as to provide instructions for the operation of device 10. For example, the user may pre-select: 1) a desired intensity of the blue light directed at desired portion 36a of brain 36; 2) a length of a treatment cycle; 3) a desired portion of the treatment cycle to which the blue light is directed at the desired portion of brain 36; 4) a number of treatment cycles to be performed and/or a desired treatment period in which the treatment cycle is repeated; and 5) other parameters associated with light delivery such as pulse width, duty cycle, etc., that are generally known in the field. In addition, it is contemplated for the user to pre-select the selected actuation of each light source 78 of the array of light sources. In other words, the user may toggle light sources 78 of the array of light sources to the on condition: 1) simultaneously; 2) sequentially; or 3) in a user selected order.

In response to the instructions provided by the user, CPU 80 executes a computer program stored thereon and provides signals along lead wire 76 to toggle each light source 78 of the array of light sources between the on condition and the off condition and to control the intensity of the blue light source supplied by each of the light sources 78. Each light source 78 of the array of light sources may be toggled simultaneously or may be toggled individually. For example, it is contemplated for CPU 80 to toggle each light source 78 of the array of light sources simultaneously to direct blue light at desired portion 36a of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours). Alternatively, CPU 80 may selectively toggle each light source 78 of the array of light sources individually so as to direct blue light at the desired portion of brain 36 at a desired intensity (e.g. between 0 and 100 mJ/cm$^2$·min) for a desired portion (e.g. 1 second) of a treatment cycle (e.g. 1 minute). The process may be repeated for a desired treatment period (e.g. 6 hours).

Various modes of carrying out the invention are contemplated as being within the scope of the following claims particularly pointing out and distinctly claiming the subject matter, which is regarded as the invention.

We claim:

1. A method of modulating brain inflammation, comprising the steps of:
    providing a support housing a light source and having flexible first and second projections projecting therefrom, wherein the light source has a first off condition and a second on condition wherein the light source generates light having a wavelength in a selected range and wherein the first and second projections having corresponding terminal ends;
    inserting the support through an opening in a cranium housing a brain such that the light source is directed at and spaced from an outer surface of the brain and such that the terminal ends of the first and second projections engage an inner surface of the cranium, the terminal ends of the first and second projections being spaced by a dimension greater than the dimension of the opening in the cranium; and
    switching of the light source to the on condition for a first portion of a treatment cycle.

2. The method of claim 1 comprising the additional step of switching of the light source from the on condition to the off condition for a second portion of the treatment cycle.

3. The method of claim 1 comprising the additional steps of repeating the step of switching of the light source to the on condition for the first portion of a treatment cycle for a plurality of treatment cycles.

4. The method of claim 1 comprising the additional step of positioning the light source at a location spaced from an outer surface of the brain.

5. The method of claim 1 comprising the additional step of positioning the light source at a location abutting an outer surface of the brain.

6. The method of claim 1 comprising the additional step of positioning the light source at a location wherein at least a portion of the light source is received within the brain.

7. The method of claim 1 wherein the light source is one of a plurality of light sources, and wherein the method further comprises the additional step of switching each of the plurality of light source to the on condition for the first portion of a treatment cycle.

8. The method of claim 7 wherein the plurality of light sources are switched simultaneously to the on condition.

9. The method of claim 8 wherein the rod includes a plurality of fenestrations extending therethrough, the plurality of fenestrations adapted for allowing the passage of nerve sprouts from the peripheral nerve therethrough.

10. The method of claim 1 wherein the support has an outer surface and is fabricated from a biocompatible polymer.

11. The method of claim 10 wherein the first projection has an outer surface and a first end interconnected to the outer surface of the support, the first projection having a generally uniform width from the first end of the first projection to the terminal end of the first projection.

12. The method of claim 11 wherein the second projection has an outer surface and a first end interconnected to the outer surface of the support, the second projection having a generally uniform width from the first end to the second projection to the terminal end of the second projection.

13. The method of claim 1 wherein the first and second projections diverge from each other as the first and second projections extend away from the outer surface of the support.

14. The method of claim 1 comprising the additional step of operatively connecting a controller to the light source, the controller providing control signals to the light source for selectively controlling the switching of the light source between the on and the off conditions.

* * * * *